United States Patent
Mitra et al.

(10) Patent No.: US 7,173,074 B2
(45) Date of Patent: *Feb. 6, 2007

(54) COMPOSITION CONTAINING A POLYMERIZABLE REDUCING AGENT, KIT, AND METHOD

(75) Inventors: Sumita B. Mitra, West Saint Paul, MN (US); Afshin Falsafi, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 327 days.

This patent is subject to a terminal disclaimer.

(21) Appl. No.: 10/121,326

(22) Filed: Apr. 12, 2002

(65) Prior Publication Data

US 2003/0166740 A1 Sep. 4, 2003

Related U.S. Application Data

(63) Continuation-in-part of application No. 10/040,962, filed on Dec. 29, 2001.

(51) Int. Cl.
- A61K 6/083 (2006.01)
- A61C 5/00 (2006.01)
- A61F 2/00 (2006.01)
- C08F 4/28 (2006.01)
- C08F 4/40 (2006.01)

(52) U.S. Cl. .................. 523/116; 523/115; 523/118; 523/120; 526/217; 526/222; 526/227; 433/228.1

(58) Field of Classification Search ............ 523/115, 523/116, 118, 120; 526/217, 222, 227; 433/228.1
See application file for complete search history.

(56) References Cited

U.S. PATENT DOCUMENTS

| | | | |
|---|---|---|---|
| 3,591,438 A | 7/1971 | Toback et al. | |
| 3,625,930 A | 12/1971 | Toback et al. | |
| 3,991,008 A * | 11/1976 | Temin et al. | 523/115 |
| 4,209,434 A | 6/1980 | Wilson et al. | |
| 4,503,169 A | 3/1985 | Randklev | |
| 4,695,251 A | 9/1987 | Randklev | |
| 4,872,936 A | 10/1989 | Engelbrecht | |
| 4,966,938 A | 10/1990 | Wang et al. | |
| 5,130,347 A | 7/1992 | Mitra | |
| 5,154,762 A | 10/1992 | Mitra et al. | |
| 5,380,772 A * | 1/1995 | Hasegawa et al. | 522/14 |
| 5,501,727 A | 3/1996 | Wang et al. | |
| 5,520,725 A | 5/1996 | Kato et al. | |
| 5,525,648 A | 6/1996 | Aasen et al. | |
| 5,554,030 A | 9/1996 | Ario et al. | |
| 5,595,487 A | 1/1997 | Ario et al. | |
| 5,814,682 A * | 9/1998 | Rusin et al. | 523/116 |
| 5,849,813 A * | 12/1998 | Oxman | 523/116 |
| 5,871,360 A | 2/1999 | Kato et al. | |
| 5,949,813 A * | 9/1999 | Hunsinger et al. | 375/142 |
| 6,982,288 B2 * | 1/2006 | Mitra et al. | 433/228.1 |
| 2003/0195273 A1 * | 10/2003 | Mitra et al. | 523/120 |

FOREIGN PATENT DOCUMENTS

| | | |
|---|---|---|
| EP | 0 629 672 | 12/1994 |
| EP | 0 802 194 | 10/1997 |
| EP | 0 896 043 | 2/1999 |
| GB | 1 456 273 | 11/1976 |
| JP | 56120610 A * | 9/1981 |
| JP | 63-25562 | 5/1988 |

OTHER PUBLICATIONS

Misra et al., "Redox Polymerization," *Prog. Polym. Sci.*, 1982, vol. 8, pp. 61-131.

* cited by examiner

*Primary Examiner*—Tae H Yoon
(74) *Attorney, Agent, or Firm*—Sean J. Edman

(57) ABSTRACT

The present invention provides a hardenable (i.e., curable by polymerization, crosslinking, ionic, or other chemical reaction) composition that includes polymerizable urea or thiourea compounds that function as reductants (i.e., reducing agents) in redox polymerization reactions.

48 Claims, No Drawings

COMPOSITION CONTAINING A POLYMERIZABLE REDUCING AGENT, KIT, AND METHOD

CROSS-REFERENCE TO RELATED APPLICATIONS

This application is a Continuation-In-Part of U.S. patent application Ser. No. 10/040,962, filed on Dec. 29, 2001, which is incorporated herein by reference.

TECHNICAL FIELD

This invention relates to hardenable (e.g., curable) compositions containing one or more polymerizable reducing agents. Such compositions are preferably dental compositions, such as cements, composites, and adhesives. This invention relates particularly to water-based dental cements.

BACKGROUND

Resin-based composite and restorative materials generally have very high cohesive strength, and accordingly are widely used in dentistry. Resin-based composite cements are utilized primarily for bonding of aesthetic appliances such as veneers, inlays, onlays, crowns, and bridges. Resin cements generally provide excellent physical properties such as high compressive and tensile strength and low wear resistance, and are often used for bonding in difficult indirect bonding situations such as non-parallel or short crown preps. Another important class of curable dental materials are water-based resin-modified ionically hardenable cements. Both the resin cements and resin-modified ionically hardenable cements come in a variety of colors. The cement color is often matched to the tooth color prior to using the cement. Over time, however, the color of the resin cement or resin-modified cement can change. As the cement color changes the presence of the aesthetic appliances becomes more apparent, which is aesthetically unacceptable. Certain additives to such compositions can improve color stability; however, some useful additives that improve color stability can increase the potential toxic and/or narcotic properties of these compositions. Thus, there is a need for compositions that are more medically acceptable.

SUMMARY OF THE INVENTION

The present invention provides a hardenable (e.g., curable by polymerization, crosslinking, ionic, or other chemical reaction) composition that includes polymerizable urea or thiourea compounds that function as reductants (i.e., reducing agents) in redox polymerization reactions. Such polymerizable reducing agents are advantageous because they can reduce the potential toxic or narcotic properties of derivatives from the urea or thiourea compounds (e.g., barbituric acid and 5-alkyl barbituric acids) because the polymerizable urea or thiourea compounds can become bound into the polymer matrix during the polymerization process. The hardenable composition can be used in a wide variety of applications, typically dental applications, and does not require the use of a curing light. Alternatively, a dental curing light can be used if desired when a photoinitiator is present in the hardenable composition.

The invention, in one embodiment, is a hardenable composition that includes: a hardenable resin system including an acid-functional component and an ethylenically unsaturated component; a polymerizable reducing agent that includes a functional group of the formula:

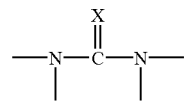

wherein X is O or S; and an oxidizing agent. For preferred embodiments, the composition can further include a secondary reducing agent.

The acid-functional component can be in the form of a monomer, oligomer, polymer, or combination thereof. Similarly, the ethylenically unsaturated component can be in the form of a monomer, oligomer, polymer, or combination thereof. The acid-functional component and the ethylenically unsaturated component can be the same component. That is, one compound can be used that has both acidic functionality and ethylenic unsaturation. Alternatively, the ethylenically unsaturated component is distinct from the acid-functional component.

The invention, in another embodiment, is a hardenable composition that includes: a hardenable resin system including an ethylenically unsaturated component; a polymerizable reducing agent that includes a functional group of the formula:

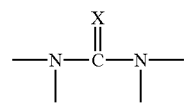

wherein X is O or S; a secondary reducing agent; and an oxidizing agent.

The invention, in another embodiment, is a hardenable composition that includes: a hardenable resin system including an ethylenically unsaturated component; a polymerizable reducing agent that includes a functional group of the formula:

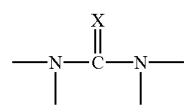

wherein X is O or S; and a non-peroxide-containing oxidizing agent.

The invention, in another embodiment, is a hardenable composition that includes: a hardenable resin system including an ethylenically unsaturated component; a polymerizable reducing agent of the formula:

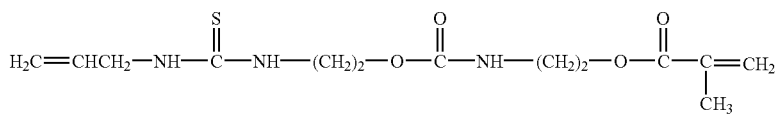

and an oxidizing agent. This reducing agent is also provided as a novel composition of matter. For preferred embodiments, the composition can further include a secondary reducing agent.

The invention, in another embodiment, is a hardenable composition that includes: a hardenable resin system including an acid-functional component and an ethylenically unsaturated component; an acid-reactive filler; a polymerizable reducing agent that includes a functional group of the formula:

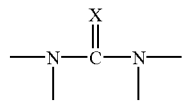

wherein X is O or S; optionally a secondary reducing agent; and an oxidizing agent.

The invention, in another embodiment, is a hardenable composition that includes: a hardenable resin system including an acid-functional component and an ethylenically unsaturated component; an acid-reactive filler; a polymerizable reducing agent that includes a functional group of the formula:

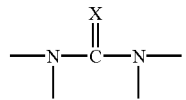

wherein X is O or S; optionally a secondary reducing agent; and an oxidizing agent.

For embodiments that include a secondary reducing agent, preferably it is an amine. The secondary reducing agent is preferably present in an amount of about 0.01 percent by weight (wt-%) to about 5.0 wt-%, based on total weight of the hardenable composition.

For embodiments in which X is oxygen (O) for the polymerizable reducing agent, the polymerizable reducing agent includes one or more urea groups. Examples of such polymerizable reducing agents include 5-acryloxyalkyl barbituric acid, 5-allyl 5-isopropyl barbituric acid, 5-ethyl 5-crotyl barbituric acid, and mixtures thereof.

For embodiments in which X is sulfur (S) for the polymerizable reducing agent, the polymerizable reducing agent includes one or more thiourea groups. Examples of such polymerizable reducing agents include 1-allyl thiourea, 1,1-diallyl thiourea, 1,3-diallyl thiourea, 1-allyl-3-(2-hydroxyethyl)-2-thiourea, a (meth)acryloxyalkyl thiourea, 1-allyl-3-methyl thiourea, and mixtures thereof.

Preferably, the oxidizing agent is selected from the group consisting of a persulfuric acid and salts thereof, peroxide, hydroperoxide, transition metal salt, perboric acid and salts thereof, permanganic acid and salts thereof, perphosphoric acid and salts thereof, and mixtures thereof. If a non-peroxide-containing oxidizing agent is used, it is preferably selected from the group consisting of a persulfuric acid salt, transition metal salt, perboric acid and salts thereof, permanganic acid and salts thereof, perphosphoric acid and salts thereof, and mixtures thereof.

Preferably, the acid-reactive filler is finely divided. Preferably, the acid-reactive filler includes a metal oxide, a metal salt, a glass, or mixtures thereof. More preferably, the acid-reactive filler includes a fluoroaluminosilicate glass. For certain embodiments, the composition can include a nonreactive filler.

The present invention also provides kits that include one or more containers whose contents collectively include the hardenable compositions described herein.

The present invention also provides methods of making and using the hardenable compositions described herein. For example, the hardenable compositions of the present invention can be used in methods of cementing (either intraorally or extraorally) a dental article (e.g., crown, bridge, orthodontic appliance) to a tooth or bone, as well as in methods of filling a tooth.

Preferably, the hardenable composition includes a glass ionomer composition that may include two or more parts in any combination of powder, liquid, or paste. The hardenable composition can be water-based, and thus can be used under moist conditions such as are typically present in the mouth.

DETAILED DESCRIPTION OF PREFERRED EMBODIMENTS

The compositions of the present invention include a hardenable resin system, a polymerizable reducing agent containing either urea or thiourea groups and their derivatives, and an oxidizing agent. Preferably, the compositions include a secondary reducing agent that can be either polymerizable or nonpolymerizable. The reducing agents and oxidizing agents are selected such that they are miscible in the compositions, and preferably, such that they are also miscible in water.

The resin system typically includes one or more ethylenically unsaturated monomers, oligomers, or polymers, as will be described below. The resin system can also include one or more acid-functional monomers, oligomers, or polymers, as will be described below. In addition, the polymerizable reducing agent can also be a polymerizable monomer, oligomer, or polymer, as will be described below.

The hardenable compositions can be used in a variety of applications, including medical and dental applications, but particularly dental applications. When used in dental applications, such as a dental adhesives, dental cements, and dental composites, the hardenable (typically, curable) composition may bond directly to dental enamel and/or dentin. Alternatively, a primer layer can be used on the dental enamel and/or dentin on which the hardenable composition is used.

The compositions of the invention can harden by undergoing one or more of a number of reactions. At least one of the mechanisms of hardening involves a redox reaction. The redox mechanism can be supplemented with a light-cure mechanism if a photoinitiator is present. Alternatively or additionally, the redox mechanism can be supplemented with an ionic hardening mechanism. By this is meant that the compositions contain ingredients that, when combined, can react via an ionic reaction to produce a hardened mass.

Resin System

The components of the resin system are selected such that they are miscible with the other components of the hardenable composition. That is, preferably, the components of the resin system are at least sufficiently miscible that they do not undergo substantial sedimentation when combined with the other ingredients of the composition (e.g., reducing agent and oxidizing agent). Preferably, the components of the resin system are miscible with water. The components of the resin system can be monomers, oligomers, polymers, or combinations thereof.

The resin systems of the hardenable compositions of the present invention typically include an ethylenically unsaturated component. Preferably, the resin systems of the hardenable compositions of the present invention also include an acid-functional component. The ethylenically unsaturated component can be present as a separate ingredient or the ethylenic unsaturation can, if desired, be present as a moiety in another compound such as the acid-functional component. In this way, one compound can include an acid-functional portion and an ethylenically unsaturated portion.

In one embodiment, the ethylenically unsaturated component includes α,β-unsaturated compounds. Preferred α,β-unsaturated compounds can provide altered properties such as toughness, adhesion, set time, and the like. When α,β-unsaturated compounds are employed, they preferably are water-soluble, water-miscible, or water-dispersible. Water-soluble, water-miscible, or water-dispersible (meth)acrylates (i.e., acrylates and methacrylates), (meth)acrylamides (i.e., acrylamides and methacrylamides), and urethane (meth)acrylates are preferred. Examples include, but are not limited to, 2-hydroxyethyl methacrylate, 2-hydroxypropyl methacrylate, tetrahydrofurfuryl methacrylate, glycerol mono- or di-methacrylate, trimethylol propane trimethacrylate, ethylene glycol dimethacrylate, triethylene glycol dimethacrylate, bisGMA, ethoxylated bisphenolA diacrylate, ethoxylated bisphenolA dimethacrylate, polyethylene glycol dimethacrylate, acrylamide, methacrylamide, methylene bis-acrylamide, methylene bis-methacrylamide, diacetone acrylamide, and diacetone methacrylamide. Suitable ethylenically unsaturated compounds are also available from a wide variety of commercial sources, such as Sigma-Aldrich, St. Louis, Mo. and Rhom and Tech, Inc., Darmstadt, Germany. Mixtures of α,β-unsaturated compounds can be used if desired.

Preferred compositions of the present invention include a sufficient quantity of ethylenically unsaturated component to provide the desired setting or hardening rate and desired overall properties following hardening. Preferably, the mixed but unset hardenable compositions of the invention contain at least about 1 percent by weight (wt-%), more preferably at least about 5 wt-%, and most preferably at least about 10 wt-%, of an ethylenically unsaturated component, based on the total weight (including water) of the hardenable (mixed but unset) composition.

The acid-functional component can include monomers, oligomers, or polymers and can include oxyacid functional derivatives of carbon, phosphorous, sulfur, and boron compounds. Suitable acid-functional compounds include those listed at column 2, line 62 through column 3, line 6 of U.S. Pat. No. 4,209,434 (Wilson et al.). Preferred acid-functional compounds are polymers, including homopolymers and copolymers (i.e., of two or more different monomers), of alkenoic acids such as acrylic acid, 2-chloroacrylic acid, 2-cyanoacrylic acid, aconitic acid, citraconic acid, fumaric acid, glutaconic acid, itaconic acid, maleic acid, mesaconic acid, methacrylic acid, and tiglic acid. Mixtures of acid-functional compounds can be used if desired.

As will be appreciated by those skilled in the art, the acid-functional component should have a molecular weight sufficient to provide good storage, handling, and mixing properties. A preferred molecular weight for a acid-functional component is about 60 to about 100,000 weight average molecular weight as evaluated using gel permeation chromatography and a polystyrene standard, with about 80 to about 30,000 being most preferred.

Preferred compositions of the present invention include a sufficient quantity of an acid-functional component to provide the desired setting characteristics and desired overall properties following hardening. Preferably, the mixed but unset hardenable compositions of the invention contain at least about 2 percent by weight (wt-%), more preferably at least about 5 wt-%, and most preferably at least about 10 wt-% of an acid-functional component, based on the total weight (including water) of the hardenable (mixed but unset) composition.

As stated above, in an alternative embodiment, the ethylenical unsaturation can be present as a moiety in the acid-functional component. For example, α,β-unsaturated acidic compounds such as glycerol phosphate monomethacrylates, glycerol phosphate dimethacrylates, hydroxyethyl methacrylate phosphates, citric acid di- or tri-methacrylates, poly(meth)acrylated oligomaleic acid, poly(meth)acrylated polymaleic acid, poly(meth)acrylated poly(meth)acrylic acid, poly(meth)acrylated polycarboxyl-polyphosphonic acid, poly(meth)acrylated polychlorophosphoric acid, poly(meth)acrylated polysulfonate, poly(meth) acrylated polyboric acid, and the like, may be used as components in the hardenable resin system. Additional compounds of this type having both acid-functional and ethylenically unsaturated components are described in U.S. Pat. No. 4,872,936 (Engelbrecht) and U.S. Pat. No. 5,130,347 (Mitra). A wide variety of such compounds containing both the ethylenically unsaturated and acid moieties can be used. Mixtures of such compounds can be used if desired.

Fillers

The hardenable compositions of the present invention can also contain fillers. Fillers may be selected from one or more of a wide variety of materials suitable for incorporation in compositions used for medical or dental applications, such as fillers currently used in dental restorative compositions, and the like. The filler is preferably finely divided. The filler can have a unimodial or polymodial (e.g., bimodal) particle size distribution. Preferably, the maximum particle size (the largest dimension of a particle, typically, the diameter) of the filler is less than about 10 micrometers, and more preferably less than about 2.0 micrometers. Preferably, the average particle size of the filler is less than about 3.0 micrometers, and more preferably less than about 0.6 micrometer.

The filler can be an inorganic material. It can also be a crosslinked organic material that is insoluble in the resin system, and is optionally filled with inorganic filler. The filler should in any event be nontoxic and suitable for use in the mouth. The filler can be radiopaque or radiolucent.

Examples of suitable inorganic fillers are naturally occurring or synthetic materials including, but not limited to: quartz; nitrides (e.g., silicon nitride); glasses derived from, for example, Ce, Sb, Sn, Ba, Zn, and Al; feldspar; borosilicate glass; kaolin; talc; titania; low Mohs hardness fillers such as those described in U.S. Pat. No. 4,695,251 (Randklev); and colloidal and submicron silica particles (e.g., pyrogenic silicas such as those available under the trade designations AEROSIL, including "OX 50", "130", "150"and "200"silicas from Degussa Corp., Akron, Ohio and CAB-O-SIL M5 silica from Cabot Corp., Tuscola, Ill.). Examples of suitable organic filler particles include filled or unfilled pulverized polycarbonates, polyepoxides, and the like.

Preferred non-acid-reactive filler particles are quartz, submicron silica, and non-vitreous microparticles of the type described in U.S. Pat. No. 4,503,169 (Randklev). Mixtures of these non-acid-reactive fillers are also contemplated, as well as combination fillers made from organic and inorganic materials.

The surface of the filler particles can also be treated with a coupling agent in order to enhance the bond between the filler and the resin. The use of suitable coupling agents include gamma-methacryloxypropyltrimethoxysilane, gamma-mercaptopropyltriethoxysilane, gamma-aminopropyltrimethoxysilane, and the like.

The filler can also be an acid-reactive filler. An acid-reactive filler is typically used in combination with an acid-functional resin component, and may or may not be used in combination with a nonreactive filler. The acid-reactive filler can, if desired, also possess the property of releasing fluoride. Suitable acid-reactive fillers include metal oxides, metal salts, and glasses. Preferred metal oxides include barium oxide, calcium oxide, magnesium oxide, and zinc oxide. Preferred metal salts include salts of multivalent cations, for example aluminum acetate, aluminum chloride, calcium chloride, magnesium chloride, zinc chloride, aluminum nitrate, barium nitrate, calcium nitrate, magnesium nitrate, strontium nitrate, and calcium fluoroborate.

Preferred glasses include borate glasses, phosphate glasses, and fluoroaluminosilicate ("FAS") glasses. FAS glasses are particularly preferred. The FAS glass preferably contains sufficient elutable cations so that a hardened dental composition will form when the glass is mixed with the components of the hardenablee composition. The glass also preferably contains sufficient elutable fluoride ions so that the hardened composition will have cariostatic properties. The glass can be made from a melt containing fluoride, alumina, and other glass-forming ingredients using techniques familiar to those skilled in the FAS glassmaking art. The FAS glass preferably is in the form of particles that are sufficiently finely divided so that they can conveniently be mixed with the other cement components and will perform well when the resulting mixture is used in the mouth. Preferably, the average particle size (typically, diameter) for the FAS glass is at least about 0.2 micrometer, and more preferably at least about 1 micrometer, as measured using, for example, a sedimentation analyzer. Preferably, the average particle size (typically, diameter) for the FAS glass is no greater than about 10 micrometers, and more preferably no greater than about 5 micrometers. Suitable FAS glasses will be familiar to those skilled in the art, and are available from a wide variety of commercial sources, and many are found in currently available glass ionomer cements such as those commercially available under the trade designations VITREMER, VITREBOND, RELY X LUTING CEMENT and KETAC-FIL (3M ESPE Dental Products, St. Paul, Minn.), FUJI II, GC FUJI LC and FUJI IX (G-C Dental Industrial Corp., Tokyo, Japan) and CHEMFIL Superior (Dentsply International, York, Pa.). Mixtures of fillers can be used if desired.

The FAS glass can optionally be subjected to a surface treatment. Suitable surface treatments include, but are not limited to, acid washing (e.g., treatment with a phosphoric acid), treatment with a phosphate, treatment with a chelating agent such as tartaric acid, and treatment with a silane or an acidic or basic silanol solution. Desirably the pH of the treating solution or the treated glass is adjusted to neutral or near-neutral, as this can increase storage stability of the hardenable composition.

In certain compositions mixtures of acid-reactive and non-acid-reactive fillers can be used either in the same part or in different parts.

The amount of filler should be sufficient to provide a hardenable composition having desirable mixing and handling properties before hardening, and good performance after hardening. Preferably, the filler represents no greater than about 90 wt-%, more preferably no greater than about 85 wt-%, and most preferably no greater than about 80 wt-%, of the total weight (including water) of the hardenable composition components. Preferably, the filler represents at least about 1 wt-%, more preferably at least about 5 wt-%, and most preferably at least about 30 wt-%, of the total weight (including water) of the hardenable composition components.

Redox Initiators

The reducing and oxidizing agents are conveniently discussed together. They should react with or otherwise cooperate with one another to produce free-radicals capable of initiating polymerization of the resin system (e.g., the ethylenically unsaturated component). This type of cure is a dark reaction, that is, it is not dependent on the presence of light and can proceed in the absence of light. The reducing and oxidizing agents are preferably sufficiently shelf-stable and free of undesirable colorization to permit their storage and use under typical dental conditions. They should be sufficiently miscible with the resin system (and preferably water-soluble) to permit ready dissolution in (and discourage separation from) the other components of the hardenable composition. Preferably, a reducing agent of the present invention has a water solubility of at least about 2 wt-% at room temperature.

The reducing agents of the present invention include a polymerizable reducing agent and optionally a secondary reducing agent, which may or may not be polymerizable. These reducing agents can be in the form of a monomer, oligomer, or polymer. The polymerizable reducing agent includes a group of the following structure,

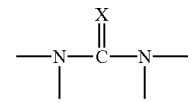

wherein X is oxygen (O) or sulfur (S). When X is O, the reducing agent includes a urea group. Alternatively, when X is S, the reducing agent includes a thiourea group. Urea and thiourea groups are known to function as reductants in oxidation-reduction (i.e., redox) polymerization reactions. In addition, derivatives of urea and thiourea are also useful as polymerizable reducing agents. Various combinations of such polymerizable reducing agents can be used if desired.

Urea compounds include, for example, derivatives of barbituric acid such as 5-acryloxyalkyl barbituric acid, 5-allyl 5-isopropyl barbituric acid, and 5-ethyl 5-crotyl barbituric acid.

Preferably, the polymerizable reducing agent includes an allyl thiourea group, as it is acid stable and prevents the formation of coloration often encountered with amine-containing reducing agents or with ascorbic acid. Preferred polymerizable reducing agents that include an allyl thiourea group include a (meth)acryloxyalkyl thiourea, 1-allyl thiourea, 1,1-diallyl thiourea, 1,3-diallyl thiourea, 1-allyl-3-(2-hydroxyethyl)-2-thiourea, and 1-allyl-3-methyl thiourea. A most preferred polymerizable reducing agent that includes an allyl thiourea group is represented by the following structure:

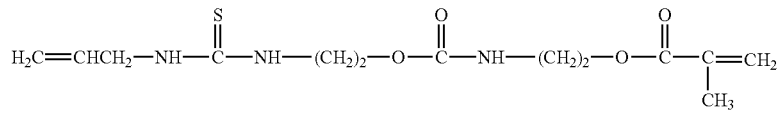

Secondary reducing agents can be either polymerizable or nonpolymerizable. Preferred secondary reducing agents include ascorbic acid, ascorbic acid derivatives, and metal complexed ascorbic acid compounds as described in U.S. Pat. No. 5,501,727 (Wang et al.); amines, especially tertiary amines, such as 4-tert-butyl dimethylaniline; aromatic sulfinic salts, such as p-toluenesulfinic salts and benzenesulfinic salts; thioureas, such as 1-ethyl-2-thiourea, tetraethyl thiourea, tetramethyl thiourea, 1,1-dibutyl thiourea, and 1,3-dibutyl thiourea; and mixtures thereof. Other secondary reducing agents may include cobalt (II) chloride, ferrous chloride, ferrous sulfate, hydrazine, hydroxylamine (depending on the choice of oxidizing agent), oxalic acid, salts of a dithionite or sulfite anion, and mixtures thereof. Preferably, the secondary reducing agent is an amine.

Typically, with the use of the polymerizable urea or thiourea reducing agent and the secondary reducing agent, significant advantages can be realized. This combination provides a balance of properties with respect to color stability of both the hardenable and hardened compositions, toxicity of the hardened composition, and reaction time ("snap set") of the hardenable composition, along with the shelf stability of the components of the hardenable composition.

Suitable oxidizing agents will also be familiar to those skilled in the art, and include but are not limited to persulfuric acid and salts thereof, such as sodium, potassium, ammonium, cesium, and alkyl ammonium salts. Additional oxidizing agents include peroxides such as benzoyl peroxides, hydroperoxides such as cumyl hydroperoxide, t-butyl hydroperoxide, sodium peroxide, hydrogen peroxide, and amyl hydroperoxide, as well as salts of transition metals such as cobalt (III) chloride and ferric chloride, cerium (IV) sulfate, perboric acid and salts thereof, permanganic acid and salts thereof, perphosphoric acid and salts thereof, and mixtures thereof.

It may be desirable to use more than one oxidizing agent or more than one reducing agents. Small quantities of transition metal compounds may also be added to accelerate the rate of redox cure.

The reducing and oxidizing agents are present in an amount sufficient to permit an adequate free-radical reaction rate. This can be evaluated by combining all of the ingredients of the hardenable composition except for the optional filler, and observing whether or not a hardened mass is obtained.

Preferably, the polymerizable reducing agent is present in an amount of at least about 0.01 wt-%, and more preferably at least about 0.1 wt-%, based on the total weight (including water) of the components of the hardenable composition. Preferably, the polymerizable reducing agent is present in an amount of no greater than about 10 wt-%, and more preferably no greater than about 5 wt-%, based on the total weight (including water) of the components of the hardenable composition.

Preferably, the optional secondary reducing agent is present in an amount of at least about 0.01 wt-%, and more preferably at least about 0.05 wt-%, based on the total weight (including water) of the components of the hardenable composition. Preferably, the optional secondary reducing agent is present in an amount of no greater than about 10 wt-%, and more preferably no greater than about 5 wt-%, based on the total weight (including water) of the components of the hardenable composition.

Preferably, the oxidizing agent is present in an amount of at least about 0.01 wt-%, and more preferably at least about 0.10 wt-%, based on the total weight (including water) of the components of the hardenable composition. Preferably, the oxidizing agent is present in an amount of no greater than about 10 wt-%, and more preferably no greater than about 5 wt-%, based on the total weight (including water) of the components of the hardenable composition.

The reducing or oxidizing agents can be microencapsulated as described in U.S. Pat. No. 5,154,762 (Mitra et al.). This will generally enhance shelf stability of the hardenable composition, and if necessary permit packaging the reducing and oxidizing agents together. For example, through appropriate selection of an encapsulant, the oxidizing and reducing agents can be combined with the acid-functional component and optional filler and kept in a storage-stable state. Likewise, through appropriate selection of a water-insoluble encapsulant, the reducing and oxidizing agents can be combined with the FAS glass and water and maintained in a storage-stable state.

Preferably the encapsulant is a medically acceptable polymer and a good film former. Also, the glass transition temperature (Tg) of the encapsulant preferably is above room temperature.

Photoinitiators

Photoinitiators can also be added to the hardenable composition, but are not required. The photoinitator should be capable of promoting free radical crosslinking of the ethylenically unsaturated component on exposure to light of a suitable wavelength and intensity. It also preferably is sufficiently shelf-stable and free of undesirable coloration to permit its storage and use under typical dental conditions. Visible light photoinitiators are preferred. The photoinitiator preferably is miscible with the resin system, and more preferably water-soluble or water-miscible. Photoinitiators bearing polar groups usually have a sufficient degree of water-solubility or water-miscibility. The photoinitiator frequently can be used alone but typically it is used in combination with a suitable donor compound or a suitable accelerator (for example, amines, peroxides, phosphorus compounds, ketones and alpha-diketone compounds).

Suitable visible light-induced and ultraviolet light-induced initiators will be familiar to those skilled in the art. Preferred visible light-induced initiators include camphorquinone, diaryliodonium simple or metal complex salts, chromophore-substituted halomethyl-s-triazines and halomethyl oxadiazoles. Particularly preferred visible light-induced photoinitiators include combinations of an alpha-diketone such as camphorquinone, and a diaryliodonium salt such as diphenyliodonium chloride, bromide, iodide or hexafluorophosphate. Preferred ultraviolet light-induced polymerization initiators include amines that are optionally polymerizable.

If employed, the photoinitiator should be present in an amount sufficient to provide the desired rate of photopolymerization. This amount will be dependent in part on the light source, the thickness of the layer of the composition to be exposed to radiant energy and the extinction coefficient of the photoinitiator.

Preferably, mixed but unset photocurable compositions of the invention include at least about 0.01 wt-%, and more preferably at least about 0.1 wt-%, based on the total weight (including water) of the hardenable (mixed but unset) composition. Preferably, mixed but unset photocurable compositions of the invention include no greater than about 5 wt-%, and more preferably no greater than about 2 wt-%, based on the total weight (including water) of the hardenable (mixed but unset) composition.

Optional Additives

The compositions of the invention preferably contain water, particularly if an acid-functional component is included. The water can be present in the product as sold, or added by the dentist just prior to use, or included as a result of contact with water in the mouth. The water can be distilled, deionized, or plain tap water. Generally, deionized water is preferred.

The amount of water should be sufficient to provide adequate handling and mixing properties and to permit the transport of ions in the filler-acid reaction. Preferably, water represents at least about 2 wt-%, and more preferably at least about 5 wt-%, of the total weight of ingredients used to form the composition. Preferably, water represents no greater than about 90 wt-%, and more preferably no greater than about 80 wt-%, of the total weight of ingredients used to form the composition. Optionally, the hardenable compositions also may contain solvents (e.g., alcohols) or diluents.

If desired, the hardenable composition of the invention can contain adjuvants such as pigments, inhibitors, accelerators, viscosity modifiers, surfactants, and other ingredients that will be apparent to those skilled in the art.

Preparation and use of the Compositions

The compositions of the present invention are adjusted to provide an appropriate balance of properties in the hardenable composition, both during the setting reaction and after the composition has hardened. These properties include the color stability, the toxicity and the reaction time ("snap set") of the cured composition, along with the shelf stability of the components of the hardenable composition. For example, the hardenable composition should preferably have a snap set of less than or equal to about two (2) minutes for a dental application. The total working time or set time of a composition (i.e., the time for a hardenable resin to cure from a liquid or paste state into a solid material under moisture and temperature conditions similar to those within an oral cavity) is preferably less than about 6 minutes, and more preferably less than about 4 minutes.

The hardenable compositions of the invention can be supplied in a variety of forms including two-part powder/liquid, paste/liquid, and paste/paste systems. Other forms employing multi-part combinations (i.e., combinations of two or more parts), each of which is in the form of a powder, liquid, gel, or paste are also possible. In a multi-part system, one part typically contains the reducing agent(s) and a second part typically contains the oxidizing agent(s). Therefore, if the polymerizable reducing agent is present in one part of the system, then the oxidizing agent is typically present in a second part of the system. However, the polymerizable reducing agent and oxidizing agent can be combined in the same part of the system through the use of the microencapsulation technique.

The components of the hardenable composition can be included in a kit, where the contents of the composition are packaged, as described below, to allow for storage of the components until they are needed.

When used as a dental composition, the components of the hardenable compositions can be mixed and clinically applied using conventional techniques. A curing light is not required (unless a photoinitiator has been included in the composition). The compositions can provide very good adhesion to dentin and/or enamel, without requiring hard tissue pretreatment. Alternatively, a primer layer can be used on the tooth tissue on which the hardenable composition is used. The compositions can also provide very good long-term fluoride release. Hence the compositions of the invention may provide glass ionomer cements that can be cured in bulk without the application of light or other external curing energy, do not require a pre-treatment, have improved physical properties including improved flexural strength, and have high fluoride release for cariostatic effect.

The compositions of the invention are particularly well adapted for use as a wide variety of dental materials, which may be filled or unfilled. They can be used in sealants or adhesives, which are lightly filled composites or unfilled compositions that are cured after being disposed adjacent to a tooth (i.e., placing a dental material in temporary or permanent bonding or touching contact with a tooth). They can be used in composites, which are typically filled compositions. They can also be used in restoratives, which are composites that are polymerized after being disposed adjacent to a tooth. They can also be used in prostheses, which are composites that are shaped and polymerized for final use (e.g., as a crown, bridge, veneer, inlay, onlay, or the like), before being disposed adjacent to a tooth. Such preformed articles can be ground or otherwise formed into a custom-fitted shape by the dentist or other user.

The compositions have particular utility in clinical applications where cure of conventional light-curable cement may be difficult to achieve. Such applications include, but are not limited to, deep restorations, large crown build-ups, endodontic restorations, attachment of orthodontic brackets (including pre-coated brackets, where, for example, a paste portion could be pre-applied to the bracket and a liquid portion could later be brushed onto a tooth), bands, buccal tubes, and other devices, luting of metallic crowns or other light-impermeable prosthetic devices to teeth, and other restorative applications in inaccessible areas of the mouth.

For preferred embodiments, the combination of an ionic hardening reaction between the FAS glass and acidic polymer, plus a separate redox curing dark reaction, facilitates thorough, uniform cure and retention of good clinical properties. The compositions of the invention thus show good promise as a universal restorative.

Objects and advantages of this invention are further illustrated by the following examples, but the particular materials and amounts thereof recited in these examples, as well as other conditions and details, should not be construed to unduly limit this invention. Unless otherwise indicated, all parts and percentages are on a weight basis and all water is deionized water.

EXAMPLES

Abbreviations:

AA:ITA Copolymer made from a 4:1 mole ratio of acrylic acid:itaconic acid, prepared according to Example 3 of U.S. Pat. No. 5,130,347 (Mitra), MW (average)=106,000; polydispersity $\rho$=4.64.

AA:IA:IEM Polymer made by reacting AA:ITA copolymer with sufficient 2-isocyanatoethyl methacrylate to convert 16 mole percent of the acid groups of the copolymer to pendent methacrylate groups, according to the dry polymer preparation of Example 11 of U.S. Pat. No. 5,130,347.

AHTU 1-Allyl-3-(2-hydroxyethyl)-2-thiourea (Sigma-Aldrich, St. Louis, Mo.).

ATU Allylthiourea (Sigma-Aldrich).

BHT Butylated hydroxytoluene (PMC Specialties, Fords, N.J.).

BisGMA 2,2-Bis[4-(2-hydroxy-3-methacryloyloxypropoxy)phenyl]propane (CAS No. 1565-94-2).

GDMA Glyceryl dimethacrylate (Rhom and Tech, Inc., Darmstadt, Germany).

HEMA 2-Hydroxyethyl methacrylate (Rhom and Tech, Inc.); contains 150 ppm 4-methoxyphenol as an inhibitor.

IEM 2-Isocyanatoethyl methacrylate (Sigma-Aldrich).

KPS Potassium persulfate (Sigma-Aldrich).

FG-KPS Finely ground potassium persulfate (Sigma-Aldrich).

MEC-KPS Microencapsulated potassium persulfate prepared according to Example 3 of U.S. Pat. No. 5,130,347.

TBDMA 4-tert-Butyl dimethylaniline (Sigma-Aldrich).

FAS I A fluoroaluminasilicate (FAS) glass powder like "Control Glass" of Example 1 of U.S. Pat. No. 5,154,762 (Mitra et al.) (but having a surface area of 2.8 m$^2$/g) was silane-treated with a liquid treatment solution. The treatment solution had been prepared by combining 4 parts A174 γ-methacryloxypropyl trimethoxysilane (CK Witco Corp., Greenwich, Conn.) and 40 parts water, adding glacial acetic acid to obtain a pH of 3.01, and stirring for 0.5 hours. The resulting clear treatment solution was mixed with 100 parts of the glass powder and an additional 67 parts of water to provide a slurry. The pH of the slurry was adjusted to 7.0 by adding 5% ammonium hydroxide. After 30 minutes of additional stirring, the mixture was poured into a tray lined with TEFLON polytetrafluoroethylene (DuPont, Wilmington, Del.) and dried for 24 hours at 95° C. The resulting dried cake was crushed by sifting it through a 60-micrometer sieve.

FAS II An FAS glass like FAS I was prepared, except that the dried cake was sifted through a 74-micrometer sieve.

FAS III The "Control Glass" of Example 1 of U.S. Pat. No. 5,154,762 was ground to a surface area of 84 m$^2$/g and silane-treated with a liquid treatment solution. The silane treatment and subsequent process for isolating the dried glass was carried out as described for FAS I, except that 8 parts of A174 γ-methacryloxypropyl trimethoxysilane were used The resulting dried cake was crushed by sifting it through a 74-micrometer sieve.

FAS IV FAS IV was like FAS I but without silane treatment.

FAS V 50/50 Blend of FAS II and FAS IV.

FAS VI Schott Glass (Product No. G 018-117, Schott Glas Export GmbH, Landshut, Germany) silane treated as described for FAS III.

Zr—Si Filler Radiopaque zirconia-silica (Zr—Si) filler was prepared as described in U.S. Pat. No. 4,503,169 (Randklev).

Test Methods:

Compressive strength (CS): Compressive strength was evaluated by first injecting a mixed cement sample into a glass tube having a 4-mm inner diameter. The ends of the glass tube were plugged with silicone plugs. The filled tubes were subjected to 0.275 megapascal (MPa) pressure for 5 minutes, placed in a chamber at 37° C. and greater than 90% relative humidity (RH) and allowed to stand for 1 hour. The cured sample was next placed in 37° C. water for 1 day, and then cut to a length of 8 mm. Compressive strength was determined according to ISO Standard 7489 using an INSTRON universal tester (Instron Corp., Canton, Mass.) operated at a crosshead speed of 1 millimeter per minute (mm/min).

Dentin Adhesion (DA): Dentin adhesion was measured according to the procedure described in U.S. Pat. No. 5,154,762, but without using any pretreatment of the dentin.

Diametral Tensile Strength (DTS): Diametral tensile strength was measured using the above-described CS procedure, but using samples cut to a length of 2 mm.

Enamel Adhesion (EA): Enamel adhesion was measured according to the procedure described in U.S. Pat. No. 5,154,762.

Flexural Strength (FS) and Flexural Modulus (FM): Flexural strength and flexural modulus were measured according to the procedure described in ISO Test Procedure 4049.

Set Time: The set time for a hardenable resin to cure from a liquid or paste state into a solid material was measured according to the following procedure. In a constant temperature and humidity room (22° C. and 50% RH), one gram each of pastes A and B were vigorously spatulated for 25 seconds. A cubic aluminum mold having a rectangular hole (10-mm long, 8-mm wide and 5-mm deep) through the center was then completely filled with the mixed paste material. The filled mold was then placed with one filled end (the bottom end) on a polyester film that covered an aluminum pad. After 45 seconds (from time of initial mixing), another polyester film was placed on the top filled end of the mold and a 400-gram standard weight was placed on top of the film. At time 90 seconds, the weight was removed and the sandwiched sample construction was transferred to a 95% RH and 37° C. humidity chamber. At time 120 seconds, the top polyester film was removed and the top surface of the curing paste material was manually indented with an indenter device consisting of a cylindrical "needle" having a flat point at one end and connected to a 400-gram block of material at the handle end. The test sample was indented every 10–15 seconds until the needle end did not hit the film-covered aluminum pad. The elapsed time from the start of mixing until the last touch of the needle with the bottom plate was defined as set time. The set time was reported an average of 2 or 3 measurements.

Working Time: The working time for a mixed paste-paste cement to solidify was measured according to the following procedure. The tools and pastes were stored before use in a constant temperature and humidity room (22° C. and 50% RH) and the procedure was conducted in the same room. Selected amounts of A and B pastes were mixed by a spatula on a pad for 25 seconds (sec) and the resulting mixed composition sample transferred into the semi-cylindrical trough section (8-cm long, 1-cm wide and 3-mm deep) of an 8-cm by 10-cm plastic block. At time 1:00 min, perpendicular grooves were made using a ball point (1-mm diameter) groove maker across the trough every 30 sec; at 2:00 min, the grooves were made every 15 see; and, closer to the end of the working time, the grooves were made every 10 sec. The end of the working time was determined when the lumps of the cement sample moved with the groove maker. The working time was reported as the average of 2 or 3 measurements.

Expansion in Water: The expansion in water of a cured resin sample was determined according to the following procedure. In a constant temperature and humidity room (22° C. and 50% RH), selected amounts of A and B pastes were mixed by a spatula on a pad for 25 sec and the resulting mixed composition samples were transferred into three 20-mm (inner diameter (ID))×1-mm deep TEFLON disk molds sandwiched between sheets of polyester film and polycarbonate plates. The filled disk molds were clamped down (400-g force) and immediately placed in a 37° C., 95% RH chamber to cure. Ten minutes after the start of mixing, one disk was removed from the mold and placed on a wet paper towel. A bisecting line was drawn on the sample with a permanent marker, and the sample was scribed on the line with a dental scaler. Any flashing from the edge of the sample was cleared, and the sample was immersed in Petri dish filled with 37° C. deionized (DI) water. This procedure was then repeated for the remaining 2 disk samples. Immediately (about 15 minutes from the start of mixing), an optical microscope was used to take 2 measurements of the length of the scribed lines for each sample while the samples were still immersed in the water. The averaged values represented the initial values (IV). After 24 hours, 2 measurements of the lengths of the scribed lines for all 3 samples were obtained and averaged to provide the expansion values (EV). Percent expansion for each sample was calculated according to the following formula: % Expansion in Water= (EV−IV)×100/IV. The percent expansion in water for the cured resin was reported as the average of the 3 sample percent expansion values.

Starting Material:

Liquid Resin A: Liquid Resin A was made by mixing AA:ITA (14.4 parts), AA:ITA:IEM (35.6 parts), HEMA (17.1 parts), water (32.9 parts), and BHT (0.06 part). The resulting solution of hardenable resin was designated as Liquid Resin A.

Examples 1–2 and Comparative Examples 1–2

Gelation Study with Liquid Resin A

Gelation studies were conducted to determine the effectiveness of different polymerizable reducing agent systems by formulating different reducing agents in various combinations with an oxidizing agent and evaluating gelation time following addition of the agents to a hardenable resin. Specifically, various reducing agents were combined with the KPS oxidizing agent and then added to Liquid Resin A with stirring at room temperature for 5–10 seconds. Gelation time was measured from the time the combined agents were added to the resin until the mixture transformed from a liquid to a viscous gel. Amounts of ingredients used, gelation time, and gel appearance are presented in Table 1.

TABLE 1

| Ex. | Liquid Resin A (g) | Oxidizing Agent (g) | Reducing Agents (g) | Gelation Time Min:Sec and Appearance |
|---|---|---|---|---|
| CE 1 | 1.14 | KPS (0.05) | ATU (0.05) | 1:55 Clear |
| 1 | 1.05 | KPS (0.045) | ATU (0.025) TBDMA (0.025) | 0:55 Clear to Milky White |

TABLE 1-continued

| Ex. | Liquid Resin A (g) | Oxidizing Agent (g) | Reducing Agents (g) | Gelation Time Min:Sec and Appearance |
|---|---|---|---|---|
| 2 | 1.05 | KPS (0.045) | AHTU (0.025) TBDMA (0.025) | 1:00 Clear |
| CE 2 | 1.20 | KPS (0.06) | TBDMA (0.06) | 3:00 Dark Pink |

The results in Table 1 show that the combination of a polymerizable reducing agent and an amine reducing agent (Examples 1 and 2) lead to a more rapid gelation time of the Liquid Resin A as compared to the polymerizable reducing agent used alone (Comparative Example 1) or the amine reducing agent used alone (Comparative Example 2).

Examples 3–6

Set Time Study with Liquid Resin A and FAS Fillers

Set time studies were conducted to determine the effectiveness of a polymerizable reducing agent in various combinations with an oxidizing agent and different fluoroaluminasilicate (FAS) glass fillers. Set times were determined following addition of the agents and fillers to a hardenable resin containing polymers of ethylenically unsaturated carboxylic acids. Such hardenable systems containing polymers of ethylenically unsaturated carboxylic acids, FAS glass fillers, and water are commonly known as glass ionomer cements. Specifically, the FAS glass fillers (containing various amounts of the oxidizing agent FG-KPS) were combined with the Liquid Resin A (containing various amounts of the polymerizable reducing agent ATU) by mixing with a spatula at room temperature for 15–30 seconds. Set times were determined according to the Test Method described herein. Amounts of ingredients used and set times are presented in Table 2.

TABLE 2

| Example | Filler | % KPS in Filler | % ATU in Liquid Resin A | Filler/ Resin A | Set Time Min:Sec |
|---|---|---|---|---|---|
| 3A | FAS II | 1 | 1 | 2.7 | 5:20 |
| 3B | FAS II | 1 | 2 | 2.7 | 4:00 |
| 3C | FAS II | 2 | 1 | 2.7 | 4:10 |
| 3D | FAS II | 2 | 2 | 2.7 | 3:00 |
| 4A | FAS VI | 1 | 1 | 2.2 | 3:45 |
| 4B | FAS VI | 1 | 2 | 2.2 | 3:35 |
| 4C | FAS VI | 2 | 1 | 2.2 | 3:30 |
| 4D | FAS VI | 2 | 2 | 2.2 | 3:15 |
| 5A | FAS VI + FAS II (1:1 Blend) | 1 | 1 | 2.5 | 4:10 |
| 5B | FAS VI + FAS II (1:1 Blend) | 1 | 2 | 2.5 | 4:05 |
| 5C | FAS VI + FAS II (1:1 Blend) | 2 | 1 | 2.5 | 3:40 |
| 5D | FAS VI + FAS II (1:1 Blend) | 2 | 2 | 2.5 | 2:50 |
| 6A | FAS V | 1 | 1 | 2.7 | 4:15 |
| 6B | FAS V | 1 | 2 | 2.7 | 3:20 |
| 6C | FAS V | 2 | 1 | 2.7 | 3:55 |
| 6D | FAS V | 2 | 2 | 2.7 | 2:20 |

The results from Table 2 show that a wide variety of compositions containing a hardenable resin, a KPS-ATU redox system, and various FAS fillers have set times acceptable for use as dental materials.

Examples 7–10

Hardenable resins (Examples 7–10) were prepared as described for Example 5D, except that the Liquid Resin A (plus 2% ATU) was aged for 1 week, 2 weeks, 4 weeks, and 8 weeks, respectively, at 37° C. and 90% RH. Following mixing of ingredients and subsequent curing the resulting solid resins were evaluated for Enamel Adhesion (EA), Compressive Strength (CS), and Diametral Tensile Strength (DTS) according to the Test Methods described herein. Results are shown in Table 3.

TABLE 3

| Example | Ageing Time of Example 5D | EA (MPa) | CS (MPa) | DTS (MPa) |
|---|---|---|---|---|
| 5D | Initial | 8.7 | 137 | 25.2 |
| 7 | 1 week | 8.0 | 146 | 24.6 |
| 8 | 2 week | 8.66 | 153 | 25.6 |
| 9 | 4 week | 9.29 | 148 | 22.5 |
| 10 | 8 week | 9.22 | 145 | 26.7 |

It can be concluded from the data in Table 3 that no significant difference in physical properties (EA, CS, or DTS) occurred as a result of ageing the Liquid Resin A (plus 2% ATU).

Example 11

A filler (powder)/liquid composition was formulated in a manner similar to Examples 3–6, except that the polymerizable reducing agent ATU was initially added to the filler rather than to the Liquid Resin A. Specifically, the filler consisted of FAS V (4.65 parts), MEC-KPS (0.5 parts), and ATU (0.2 parts). The filler was added to Liquid Resin A at a ratio of 2.5:1 and the resulting set time was 2 minutes, 5 seconds. Physical properties were determined according to the Test Methods described herein and found to be as follows: CS was 115 MPa, DTS was 22.1 MPa, and EA (without conditioning) was 6.08 MPa.

Examples 12–13

A paste/paste composition (glass ionomer cement systems) was formulated by using a spatula to mix for 25 seconds Paste 75A (1.4 g) with Paste 75B (1.0 g) to afford after curing a hardened resin cement (Example 12). Similarly, Paste 77A (1.7 g) and Paste 77B (1.0 g) were mixed to afford after curing a hardened resin cement (Example 13). The components of Pastes 75A/77A and Pastes 75B/77B are provided in Table 4 and Table 5, respectively. Set time, working time, and various physical properties of the hardened resin cements were determined according to the Test Methods described herein with results provided in Table 6.

TABLE 4

| Components | Paste 75A (Parts) | Paste 77A (Parts) |
|---|---|---|
| Water | 6.27 | 6.36 |
| HEMA | 14.25 | 14.15 |
| GDMA | 1.71 | 0.0 |
| BisGMA | 0.0 | 1.73 |
| ATU | 2.05 | 0.52 |
| TBDMA | 0.0 | 0.21 |
| FAS II | 37.06 | 37.56 |
| FAS III | 37.06 | 37.56 |
| TiO$_2$ (Degussa, Germany) | 0.46 | 0.46 |
| Fumed silica, Aerosil R812S (Degussa, Germany) | 1.14 | 1.15 |

TABLE 5

| Components | Paste 75B (Parts) | Paste 77B (Parts) |
|---|---|---|
| Water | 18.75 | 22.04 |
| HEMA | 9.40 | 7.35 |
| AA:ITA:IEM | 34.38 | 34.18 |
| BHT | 0.03 | 0.03 |
| KPS | 0.0 | 4.34 |
| MEC-KPS | 5.23 | 0.0 |
| Zr-Si filler | 32.21 | 31.07 |
| Fumed silica, Aerosil R812S | 0.0 | 0.99 |

TABLE 6

| Property | Example 12 Cement (Paste 75A + 75B) | Example 13 Cement (Paste 77A + Paste 77B) |
|---|---|---|
| CS, MPa (SD) | 120 (17) | 138 (13) |
| DTS, MPa (SD) | 23 (3) | 23 (2) |
| FS, MPa (SD) | 20 (1) | 28 (3) |
| FM, GPa (SD) | 1.6 (0.1) | 2.1 (0.1) |
| DA, MPa (SD) | 2.8 (2) | 4.0 (2) |
| BA, MPa (SD) | 7.6 (2) | 10.5 (3) |
| Working Time, min:sec | 2:20 | 3:30 |
| Set Time, min:sec | 2:20 | 3:20 |
| Expansion in Water, % | 0.8 | 1.8 |

The results from Table 6 show that paste/paste compositions containing hardenable resin systems, fillers, and a KPS-ATU redox system (in which the KPS was in one paste and the ATU was in the other paste), and have set times and physical properties acceptable for use as dental materials. The faster working and set times observed for Example 12 are attributed to a much higher level of the polymerizable reducing agent, ATU.

Example 14

Synthesis of Methacryloyl Derivative of ATU and its use as a Reductant

AHTU (8.01 grams (g), 0.05 moles) was dissolved in dry THF (100 milliliters (ml)) in a round-bottomed flask and dibutyltin dilaurate (0.20 ml; Sigma-Aldrich) was added. The flask was attached to a reflux condenser capped with a drying tube containing DRIERITE drying agent. IEM (7.75 g, 0.05 mole) was added dropwise over a period of 10 minutes at room temperature. The reaction mixture was then allowed to stir for 15 hours at 40° C. The flask was removed from the heat, and the solvents were removed by rotary evaporation to afford a colorless, viscous liquid. Infrared characterization of the product was consistent with a methacrylated-AHTU (M-AHTU) chemical structure.

Liquid Resin A was formulated with 3% by weight of M-AHTU, prepared as described above, and the resulting liquid combined with the powder used in Example 5D. Set time of the powder/liquid mixture was determined to be 3 minutes, 40 seconds.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A hardenable composition comprising:
   a hardenable resin system comprising an acid-functional component and an ethylenically unsaturated component;
   a polymerizable reducing agent comprising a thiourea group;
   a secondary reducing agent different from the polymerizable reducing agent comprising a thiourea group; and
   an oxidizing agent.

2. The composition of claim 1 wherein the secondary reducing agent is nonpolymerizable.

3. The composition of claim 1 wherein the acid-functional component and ethylenically unsaturated component are the same component.

4. The composition of claim 3 wherein the acid-functional component and ethylenically unsaturated component comprise an $\alpha,\beta$-unsaturated acidic compound selected from the group consisting of glycerol phosphate monomethacrylates, glycerol phosphate dimethacrylates, hydroxyethyl methacrylate phosphates, citric acid di- or tri-methacrylates, poly(meth)acrylated oligomaleic acid, poly(meth)acrylated polymaleic acid, poly(meth)acrylated poly(meth)acrylic acid, poly(meth)acrylated polycarboxyl-polyphosphonic acid, poly(meth)acrylated polychlorophosphoric acid, poly(meth)acrylated polysulfonate. poly(meth)acrylated polyboric acid, and mixtures thereof.

5. The composition of claim 1 wherein the ethylenically unsaturated component is distinct from the acid-functional component.

6. The composition of claim 5 wherein the ethylenically unsaturated component is selected from the group consisting of an acrylate, a methacrylate, an acrylamide, a methacrylamide, a urethane acrylate, a urethane methacrylate, and mixtures thereof.

7. The composition of claim 6 wherein the ethylenically unsaturated component is selected from the group consisting of 2-hydroxyethyl methacrylate, 2-hydroxypropyl methacrylate, tetrahydrofurfuryl methacrylate, glycerol mono- or di-methacrylate, trimethylol propane trimethacrylate, ethylene glycol dimethacrylate, triethylene glycol dimethacrylate, bisGMA, ethoxylated bisphenolA diacrylate, ethoxylated bisphenolA dimethacrylate, polyethylene glycol dimethacrylate, urethane methacrylates, acrylamide, methacrylamide, methylene bis-acrylamide, methylene bis-methacrylamide, diacetone acrylamide, diacetone methacrylamide, and mixtures thereof.

8. The composition of claim 1 wherein the acid-functional component comprises a homopolymer or copolymer of alkenoic acids.

9. The composition of claim 1 wherein the polymerizable reducing agent is selected from the group consisting of a (meth)acryloxyalkyl thiourea, 1-allyl thiourea, 1,1 -diallyl thiourea, 1,3-diallyl thiourea, 1-allyl-3-(2-hydroxyethyl)-2-thiourea, 1 -allyl-3methyl thiourea, and mixtures thereof.

10. The composition of claim 1 wherein the oxidizing agent is selected from the group consisting of persulfuric acid, persulfuric acid salt, peroxide, hydroperoxide, transition metal salt, perboric acid, perboric acid salt, permanganic acid, permanganic acid salt, perphosphoric acid, perphosphoric acid salt, and mixtures thereof.

11. The composition of claim 1 further comprising a photoinitiator.

12. The composition of claim 1 farther comprising a finely divided acid-reactive filler.

13. The composition of claim 12 wherein the filler is selected from the group consisting of a metal oxide, a metal salt, a glass, and mixtures thereof.

14. The composition of claim 13 wherein the filler comprises a fluoroaluminosilicate glass.

15. The composition of claim 1 wherein at least one of the agents of the composition is microencapsulated.

16. The composition of claim 1 wherein the hardenable resin system comprises at least about 5 wt-% of an acid-functional component and at least about 5 wt-% of an ethylenically unsaturated component, based on the total weight of the hardenable composition.

17. The composition of claim 1 wherein the polymerizable reducing agent is present in an amount of about 0.01 wt-% to about 10 wt-%, based on the total weight of the hardenable composition.

18. The composition of claim 1 wherein the oxidizing agent is present in an amount of about 0.01 wt% to about 10 wt-%, based on the total weight of the hardenable composition.

19. The composition of claim 1 wherein the composition bonds directly to dental enamel and/or dentin.

20. The composition of claim 1 in the form of a multi-part system having the polymerizable reducing agent in a first part and the oxidizing agent in a second part.

21. The composition of claim 20 wherein the multi-part system comprises at least one paste, liquid, powder, or gel part.

22. The composition of claim 21 in the form of a paste/paste, a paste/liquid, or a powder/liquid system.

23. A hardenable composition comprising:
   a hardenable resin system comprising an ethylenically unsaturated component;
   a polymerizable reducing agent comprising a thiourea group;
   a secondary reducing agent different from the polymerizable reducing agent comprising a thiourea group; and
   an oxidizing agent.

24. The hardenable composition of claim 23 wherein the secondary reducing agent is an amine.

25. The hardenable composition of claim 23 wherein the secondary reducing agent is present in an amount of about 0.05 wt-% to about 10 wt-%, based on the total weight of the hardenable composition.

26. The composition of claim 23 wherein the polymerizable reducing agent is selected from the group consisting of a (meth)acryloxyalkyl thiourea, 1-allyl thiourea, 1,1-diallyl thiourea, 1,3-diallyl thiourea, 1-allyl-3-(2-hydroxyethyl)-2-thiourea, 1-allyl-3-methyl thiourea, and mixtures thereof.

27. A hardenable composition comprising:
   a hardenable resin system comprising an acid-functional component and an ethylenically unsaturated component;
   an acid-reactive filler;
   a polymerizable reducing agent comprising a thiourea group;

secondary reducing agent different from the polymerizable reducing agent comprising a thiourea group; and an oxidizing agent.

28. The composition of claim 27 further comprising a nonreactive filler.

29. The composition of claim 27 wherein the acid-reactive filler is finely divided.

30. The composition of claim 29 wherein the filler is selected from the group consisting of a metal oxide, a metal salt, a glass, and mixtures thereof.

31. The composition of claim 30 wherein the filler comprises a fluoroaluminosilicate glass.

32. The composition of claim 27 further comprising a photoinitiator.

33. The composition of claim 27 wherein at least one of the agents of the composition is microencapsulated.

34. The composition of claim 27 wherein the acid-functional component and the ethylenically unsaturated component are the same component.

35. The composition of claim 27 wherein the ethylenically unsaturated component is distinct from the acid-functional component.

36. The composition of claim 27 wherein the ethylenically unsaturated component is selected from the group consisting of an acrylate, a methacrylate, an acrylamide, a methacrylamide, a urethane acrylate, a urethane methacrylate, and mixtures thereof.

37. The composition of claim 27 wherein the hardenable resin system comprises at least about 5 wt-% of an acid-functional component and at least about 5 wt-% of an ethylenically unsaturated component, based on the total weight of the hardenable composition.

38. The composition of claim 27 wherein the polymerizable reducing agent is present in an amount of about 0.01 wt-% to about 10 wt-%, based on the total weight of the hardenable composition.

39. The composition of claim 27 wherein the oxidizing agent is present in an amount of about 0.01 wt-% to about 10 wt-%, based on the total weight of the hardenable composition.

40. A kit comprising one or more containers whose contents collectively comprise:
   a hardenable resin system comprising an acid-functional component and an ethylenically unsaturated component;
   a polymerizable reducing agent comprising a thiourea group;
   a secondary reducing agent different from the polymerizable reducing agent comprising a thiourea group; and
   an oxidizing agent.

41. The kit of claim 40 wherein the secondary reducing agent is selected from the group consisting of ascorbic acid, ascorbic acid derivatives, metal complexed ascorbic acid compounds, amines, aromatic sulfinic salts, thioureas, cobalt (II) chloride, ferrous chloride, ferrous sulfate, hydrazine, hydroxylamine, oxalic acid, salts of a dithionite or sulfite anion, and mixtures thereof.

42. A kit comprising one or more containers whose contents collectively comprise:
   a hardenable resin system comprising an ethylenically unsaturated component;
   a polymerizable reducing agent comprising a thiourea group;
   a secondary reducing agent different from the polymerizable reducing agent comprising a thiourea group; and
   an oxidizing agent.

43. A kit comprising one or more containers whose contents collectively comprise:
   a hardenable resin system comprising an acid-functional component and an ethylenically unsaturated component;
   an acid-reactive filler;
   a polymerizable reducing agent comprising a thiourea group;
   a secondary reducing agent different from the polymerizable reducing agent comprising a thiourea group; and
   an oxidizing agent.

44. A method of making a hardenable composition, the method comprising:
   providing a resin system comprising an acid-functional component and am ethylenically unsaturated component;
   providing a polymerizable reducing agent comprising a thiourea group;
   optionally providing an acid-reactive filler;
   providing a secondary reducing agent different from the polymerizable reducing agent comprising a thiourea group;
   providing an oxidizing agent; and
   mixing the resin system, the reducing agent, the optional acid-reactive filler, the optional secondary reducing agent, and the oxidizing agent to form the composition.

45. A method of making a hardenable composition, the method comprising:
   providing a hardenable resin system comprising an ethylenically unsaturated component;
   providing a polymerizable reducing agent comprising a thiourea group;
   providing a secondary reducing agent different from the polymerizable reducing agent comprising a thiourea group;
   providing an oxidizing agent; and
   mixing the resin system, the reducing agent, the secondary reducing agent, and the oxidizing agent to form the composition.

46. A method of cementing a dental article to a tooth or bone, the method comprising:
   providing a dental article;
   providing a hardenable composition comprising:
      a resin system comprising an acid-functional component and an ethylenically unsaturated component;
      a polymerizable reducing agent comprising a thiourea group;
      an optional acid-reactive filler;
      a secondary reducing agent different from the polymerizable reducing agent comprising a thiourea group; and
      an oxidizing agent; and
   cementing the dental article to the tooth or bone using the hardenable composition.

47. A method of filling a tooth, the method comprising:
   providing a hardenable composition comprising:
      a resin system comprising an acid-functional component and an ethylenically unsaturated component;
      a polymerizable reducing agent comprising a thiourea group;
      an optional acid-reactive filler;
      a secondary reducing agent different from the polymerizable reducing agent comprising a thiourea group; and
      an oxidizing agent; and
   applying the hardenable composition to the tooth.

48. The composition of claim 1 wherein the polymerizable reducing agent comprising a thiourea group is a compound of the formula:
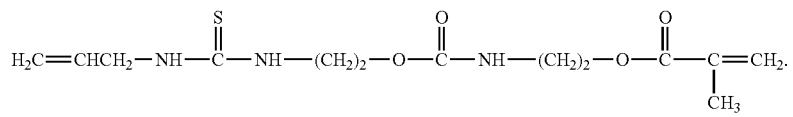

UNITED STATES PATENT AND TRADEMARK OFFICE
CERTIFICATE OF CORRECTION

PATENT NO. : 7,173,074 B2
APPLICATION NO. : 10/121326
DATED : February 6, 2007
INVENTOR(S) : Sumita B. Mitra It is certified that error appears in the above-identified patent and that said Letters Patent is hereby corrected as shown below:

<u>Column 14</u>
Line 65, delete "see;" and insert in place thereof --sec;--.

<u>Column 18,</u>
In Table 6 (6th entry) approximately line 33, delete "BA," and insert in place thereof --EA,--.

<u>Column 19,</u>
Line 38, delete "polysulfonate." and insert in place thereof --polysulfonate,--.
Line 67, delete "1-allyl-3methyl" and insert in place thereof --1-allyl-3-methyl--.

<u>Column 20,</u>
Line 9, delete "farther" and insert in place thereof --further--.
Line 28, delete "wt%" and insert in place thereof --wt-%--.

<u>Column 21,</u>
Line 1, before "secondary" insert --a--.

<u>Column 22,</u>
Line 15, delete "am" and insert in place thereof --an--.

Signed and Sealed this

Twenty-fourth Day of April, 2007

JON W. DUDAS
*Director of the United States Patent and Trademark Office*